United States Patent [19]

Kamerling

[11] Patent Number: 4,601,721
[45] Date of Patent: Jul. 22, 1986

[54] POSTERIOR CHAMBER INTRA-OCULAR DEVICE

[76] Inventor: William Kamerling, 507 Fireside La., Cherry Hill, N.J. 08003

[21] Appl. No.: 651,006

[22] Filed: Sep. 17, 1984

[51] Int. Cl.⁴ .............................................. A61F 2/16
[52] U.S. Cl. ...................................................... 623/6
[58] Field of Search .................................. 3/13; 623/6

[56] References Cited

U.S. PATENT DOCUMENTS

| | | | |
|---|---|---|---|
| 4,159,546 | 7/1979 | Shearing | 3/13 |
| 4,242,760 | 1/1981 | Rainin | 3/13 |
| 4,298,994 | 11/1981 | Clayman | 623/6 |
| 4,366,582 | 1/1983 | Faulkner | 3/13 |
| 4,476,591 | 10/1984 | Arnott | 3/13 |

OTHER PUBLICATIONS

AM Intra-Ocular Implant Soc. J.—vol. V, Oct. 1979, p. 357 (Simcoe Lenses shown in FIG. 1).
The Hoffer Ridge Lenses from Cilco (advertisement) 6 pages, Cilco, Inc. 1616 13th Ave., Box 1680, Huntington, West Va., 25717, Mar. 1983.
Ioptex literature dated Jun. 1983.
Precision-Cosmet literature dated 1984.

Primary Examiner—Ronald L. Frinks
Attorney, Agent, or Firm—Seidel, Gonda, Goldhammer & Abbott

[57] ABSTRACT

A posterior chamber intra-ocular lens has first and second flexible loops attached thereto. The arcuate distance between the attachments of the loops to the lens is not more than about 90°.

5 Claims, 5 Drawing Figures

POSTERIOR CHAMBER INTRA-OCULAR DEVICE

BACKGROUND OF THE INVENTION

Intra-ocular devices for insertion in the posterior chamber of an eye are known and generally are used to replace a cataract lens which has been removed by surgery. The intraocular lenses used today are divided into two categories, namely anterior and posterior chamber lenses. In order to insert a posterior chamber lens, the posterior capsule of the cataract must be left in the eye at the time of the cataract surgery to act as a barrier between the intra-ocular lens and the vitreous and thereby provide a barrier to prevent the lens from dislocating back into the vitreous and retina of the posterior segment of the eye.

A known device has first and second loops attached to a lens adjacent a periphery of the lens. The points of attachment of the loops to the lens are 180° apart. Surgeons have had difficulty positioning the device so that it is disposed in the desired compartment behind the iris. Insertion of the inferior loop through the incision and into the desired compartment is fairly routine. The problem is the superior loop which can wind up in either the capsular bag or in the ciliary sulcus. Due to the location where the loops are attached to the lens, I perceive that there would be less difficulty in getting both loops behind the iris and into the desired compartment if the loops were constructed and attached to the lens as disclosed herein.

SUMMARY OF THE INVENTION

The present invention is directed to an intra-ocular device for implantation in the posterior chamber of an eye. The device includes a lens having first and second flexible loops each attached to the lens adjacent the periphery thereof. The loops are adapted to position the lens in the posterior chamber of an eye. The arcuate distance between the attachment of the loops to the lens is not more than about 90°.

It is an object of the present invention to provide an intra-ocular device for implantation into the posterior chamber of an eye in a manner which provides greater certainty that both loops with be located in the capsular bag or the sulcus groove.

Other objects and advantages of the present invention will appear hereinafter.

For the purpose of illustrating the invention, there is shown in the drawings a form which is presently preferred; it being understood, however, that this invention is not limited to the precise arangements and instrumentalities shown.

DETAILED DESCRIPTION

Figure 1:
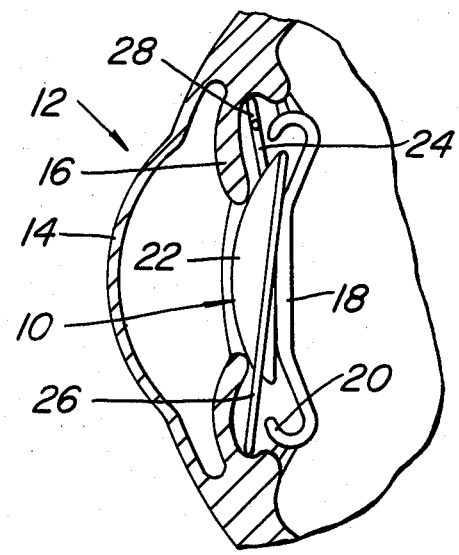
FIG. 1 is a sectional view through an eye showing a device in accordance with the present invention implanted by sulcus fixation in the posterior chamber.

Referring to the drawing in detail, wherein like numerals indicate like elements, there is shown in FIG. 1 a device in accordance with the present invention designated generally as 10 and implanted in the posterior chamber of an eye. As is well known, the eye 12 includes a cornea behind which is located an iris 16 having a centrally disposed opening. Between the iris 16 and a capsular bag 18 there is provided the posterior chamber. The capsular bag 18 has a peripheral rim 20.

The device 10 includes a lens 22 which is circular and has a peripheral rim 23. The front face of the lens 22 is convex. The rear face of the lens 22 has a planar rim portion with the major surface thereof being concave. Lens 22 is preferably made from a transparent polymeric plastic material such as polymethylmethacrylate which is crystaline, transparent and inert.

Figure 2:
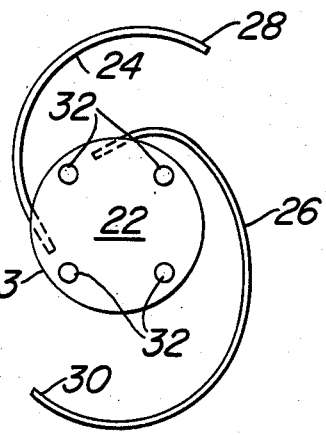
FIG. 2 is a front plan view of the device.

The lens 22 is provided with an inferior haptic loop 24 and a superior haptic loop 26. The loops 24 and 26 are flexible and are preferably made from a polymeric plastic material such as polypropylene. Each of the loops 24 and 26 has one end fixedly attached to the lens 22 and preferably at the rim 23 in any conventional manner. Loop 24 has a free end 28 and loop 26 has a free end 30. The loops 24 and 26 are preferably not the same length and are attached to the lens 22 at a location whereby the attachments are spaced from one another by an arcuate distance of approximately 90°. As shown in FIG. 2, loop 26 is longer than loop 24.

The terminal free end portion of loop 24 overlaps a small portion of loop 26 at the location where the latter is attached to the lens 22. The free ends 28 and 30 are preferably uniformly spaced from the periphery of lens 22. Lens 22 is preferably provided with a hole 32 at the clock positions of 1:30, 4:30, 7:30 and 11:30.

Figures 3, 4:
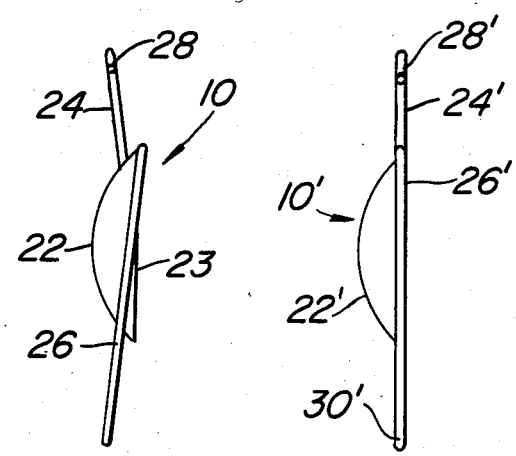
FIG. 3 is a right side view of the device shown in FIG. 2.
FIG. 4 is a view similar to FIG. 3 but showing another embodiment of the present invention.

Referring to FIG. 3, it will be noted that the loops 24 and 26 are angled forwardly at an angle of approximately 10° with respect to the plane of the rear peripheral surface of the lens 22. In FIG. 4 there is illustrated another embodiment of the present invention designated generally as 10'. In connection with device 10', the loops 24' and 26' are in a common plane parallel to the plane of the rear peripheral surface of the lens 22'.

Figure 5:
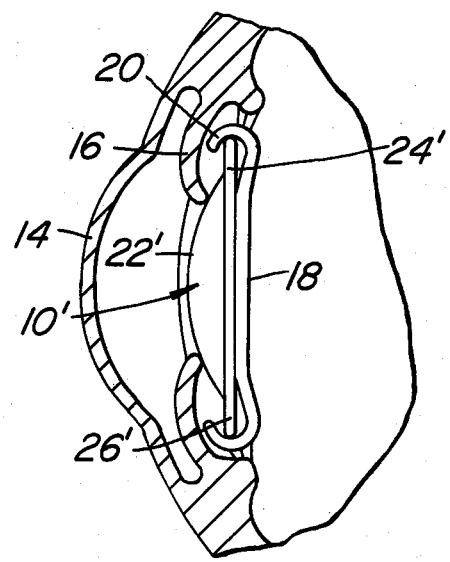
FIG. 5 is a view similar to FIG. 1, but with capsular fixation.

In FIG. 1, the device 10 is shown implanted in the small sulcus groove immediately behind the iris 16 and is generally referred to as sulcus fixation. It is within the scope of the present invention to implant the device 10 in a manner so that the loops 24 and 26 are within the rim 20 of the capsular bag 18 as shown in FIG. 5. The type of fixation is a matter of choice by a surgeon. Whichever compartment is chosen, both loops should be in the same compartment.

As a result of the shape of the loops and the location where they are attached to the lens 22, implantation is more easily attained with greater certainty that both loops will be at the desired location within the posterior chamber. Many surgeons believe the ideal location for both loops is in the capsular bag since there is greater safety and better fixation. While it is easy to insert the inferior loop of a prior art device into the capsular bag, it is difficult to also position the superior loop in the capsular bag whereby both loops are in the capsular bag.

During insertion of the device 10, loop 24 is moved through the incision by means of an appropriate instrument and rotates counterclockwise in FIG. 2 approximately 90°. When the loop 24 has been inserted, a portion of loop 26 is already in the same preselected compartment whereby the remainder of loop 26 will automatically follow after loop 24 during insertion. Lens 22 may then be dialed by inserting a tool in one of the holes 32 while the lens 22 is in the preselected compartment whether it be the sulcus groove as shown in FIG. 1 or the capsular bag 18 as shown in FIG. 5.

While the lens 22 is preferably concave-convex, it may also be plano convex and preferably has a diameter of about 6 mm. The preferred maximum transverse dimension is 13.5 mm as measured along an imaginery line corresponding to the 12 o'clock position on loop 24 and the 6 o'clock position on loop 26 in FIG. 2. The primary advantage of the device 10 is the increased certainty that when lens 22 is implanted both loops 24 and 26 will be disposed within the predetermined posterior compartment as shown in FIG. 1 or FIG. 5.

The present invention may be embodied in other specific forms without departing from the spirit or essential attributes thereof and, accordingly, reference should be made to the appended claims, rather than to the foregoing specification, as indicating the scope of the invention.

I claim:

1. An intra-ocular device for implantation in the posterior chamber of an eye comprising a lens having first and second flexible loops each attached to said lens, the second loop being longer than the first loop and the free ends of said loops being approximately 180° apart so that the loops are adapted to secure the lens in the posterior chamber of an eye, and the arcuate distance between the locations at which the loops are attached to the lens being about 90° so that when the first loop is positioned in a preselected compartment in the posterior chamber of the eye at least a portion of the second loop proximal its location of attachment to the lens is also positioned in the same compartment whereby the remaining portion of the second loop can enter the compartment by rotating the lens.

2. A device in accordance with claim 1 wherein one of said loops terminates at a free end portion which partially overlaps the other loop in the region where the other loop is attached to the lens so that when the first loop is positioned in a preselected compartment the second loop will be partially disposed in the same compartment.

3. An intra-ocular device for implantation in the posterior chamber of an eye comprising a transparent inert lens having first and second flexible loops attached thereto each terminating in a free end, the points of attachment of said loops to said lens being spaced an arcuate distance not more than about 90°, the second loop being longer than the first loop and the free ends of said loops being approximately 180° apart so that the loops are adapted to secure the lens in the posterior chamber of an eye, and a free end portion of said first loop partially overlapping a portion of the second loop where the latter is attached to said lens and radially outward therefrom, so that when the first loop is positioned in a preselected compartment in the posterior chamber of the eye at least a portion of the second loop proximal its location of attachment to the lens is also positioned in the same compartment whereby the remaining portion of the second loop can enter the compartment by rotating the lens.

4. A device in accordance with claims 1 or 3 wherein said loops lie in a common plane.

5. A device in accordance with claims 1 or 3 wherein said loops lie in converging planes and are tilted forwardly by an angle not more than about 10° so that the included angle is not less than about 160°.

* * * * *